(12) United States Patent (10) Patent No.: US 8,920,354 B2
Liberson (45) Date of Patent: Dec. 30, 2014

(54) DEVICE AND METHOD FOR TREATING INGROWN NAILS

(75) Inventor: Aharon Liberson, Haifa (IL)

(73) Assignee: Toe Fix Ltd., Haifa (IL)

( * ) Notice: Subject to any disclaimer, the term of this patent is extended or adjusted under 35 U.S.C. 154(b) by 763 days.

(21) Appl. No.: 12/282,241

(22) PCT Filed: Mar. 8, 2007

(86) PCT No.: PCT/IL2007/000296
§ 371 (c)(1),
(2), (4) Date: Sep. 9, 2008

(87) PCT Pub. No.: WO2007/102156
PCT Pub. Date: Sep. 13, 2007

(65) Prior Publication Data
US 2009/0048551 A1 Feb. 19, 2009

Related U.S. Application Data

(60) Provisional application No. 60/780,756, filed on Mar. 9, 2006.

(51) Int. Cl.
*A61F 5/11* (2006.01)
(52) U.S. Cl.
CPC .................................... *A61F 5/11* (2013.01)
USPC ............................................ 602/31; 128/882
(58) Field of Classification Search
CPC ........................................................ A61F 5/11

USPC ........ 128/893, 882; 602/30–31; 132/73, 73.5, 132/75.8, 76.2; 36/132, 136, 141, 196
See application file for complete search history.

(56) References Cited

U.S. PATENT DOCUMENTS

| | | | | |
|---|---|---|---|---|
| 1,708,716 | A | * | 4/1929 | Andersen ........................ 602/31 |
| 3,229,690 | A | * | 1/1966 | Scholl ............................ 128/894 |
| 4,057,055 | A | * | 11/1977 | Clark .............................. 602/31 |
| 4,068,656 | A | | 1/1978 | Barmore |
| 4,674,486 | A | | 6/1987 | Hoffman |
| 5,613,503 | A | | 3/1997 | Penner |
| 5,938,030 | A | | 8/1999 | Stolz |
| 8,337,443 | B2 | | 12/2012 | Harada |

FOREIGN PATENT DOCUMENTS

| | | | |
|---|---|---|---|
| EP | 2025309 | | 2/2009 |
| JP | 4324638 | | 9/2009 |
| JP | 20132300290 | A * | 11/2013 |
| KR | 962457 | | 6/2010 |
| WO | 2008/142880 | | 11/2008 |

* cited by examiner

*Primary Examiner* — Patricia Bianco
*Assistant Examiner* — Camtu Nguyen
(74) *Attorney, Agent, or Firm* — Soroker-Agmon (57) ABSTRACT

An adjustable and controllable device for treating ingrown nail comprises a releasing portion adapted to be connected to the ingrown nail plate surface and an adjustable portion adapted to exert changeable force on the releasing portion so as to elevate portions of the nail plate surface. The force that is exerted can be mechanical, magnetic, piezoelectric or any other force. A method is also provided.

2 Claims, 12 Drawing Sheets

DEVICE AND METHOD FOR TREATING INGROWN NAILS

CROSS-REFERENCE TO RELATED APPLICATION

This application claims the benefit of U.S. provisional application Ser. No. 60/780,756 filed Mar. 9, 2006.

FIELD OF THE INVENTION

The present invention relates to treating ingrown nails. More particularly, the present invention relates to adjustable device and method for rapid conservative-based treatment of ingrown toenail.

BACKGROUND OF THE INVENTION

Ingrown toenail is one of the most often problems of toenails. Recent researches in the US prove that at least 0.1% of the general population suffer from ingrown toenail. This type of deformation cause a painful infectious complication, and may lead to the development of secondary deep infection (especially dangerous for diabetic and immune deficit patients) and pressure sensitivity of the toes with limitation of activity and worsening (detriment) of life quality.

In common knowledge, there are surgical methods for treating ingrown nails (I.N.) that include total nail plate removal or partial resection of nail plate. Those methods demand surgical intervention, and anesthesia with all associated risks. The problems of currently used methods are as follows:
1) risk of operational complications that are especially dangerous in diabetic and immune deficit patients;
2) painful procedures that as a result of the necessity of anesthesia can be consequent in local or general known risks and complications;
3) hypersensitivity of the uncovered nail bed until the new toenail grows;
4) necessity of regular dressing until the new toenail grows;
5) possibility of relapses and postoperative nail deformities.

A modified technique of operation was developed that includes the resection of the deformed part of the ingrown toenail and sinus of the toenail and sewing the remaining part of the toenail and boundary skin. This is aimed at avoiding the hypersensitivity pointed out in point no. 3 and decreases the necessity of dressing pointed out in point no. 4.

Descriptions of operational methods of conservative I.N. treatment are available and are based on elastic wire application. Wire that is prepared in a stressed state is placed in the nail plate part. During a period of time, the wire restores the ingrown part to normal position. Restrictions of the method lay in its technology. The stress applied with the forces of the wire is maximal in the beginning of the treatment and streaming to zero approaching to its end. High range of forces may lead to pain and nail destruction. Deformity correction is performed during nail growth that in turn demands long period of time. This method is invasive, which is a major disadvantage.

Non-invasive methods aimed at lifting the nail of the toe are available also. Nail correction strips are described in U.S. Pat. No. 5,938,030 "Packaging arrangement for nail correction strips" by Stolz. The strips are adhered onto the surface of the nail. Hoffman in U.S. Pat. No. 4,674,486 "Method of correcting ingrown toenail" discloses a resilient sheet of fibrous reinforced material that is adhered to the nail's surface. The material is fracturable in the direction cross-wise of the direction of growth of the nail and bending the lateral edges of the material downwardly to contact and adhere to the side edges of the toenail. When in place, the material urges the side edges of the toenail upwardly.

Other devices are disclosed that depicts an insert. In U.S. Pat. No. 4,068,656 "Orthopedic toenail device" by Barmore it is described a device comprising an insert means adapted to be positioned under the nail edges adjacent the forward portion of the nail and the resilient member coacting with the insert means and acting on the top portion of the nail and biasing the insert means into and against the nail underside edges. Another device is disclosed in U.S. Pat. No. 5,613,503 "Device and method for treating ingrawing toe nails" by Panner that describes a device comprising an upper member and a lower member interconnected by an interconnecting portion interconnecting the portions only in the center. A pair of wings is provided that are curved rearwardly and downwardly for engaging the upper and lower surfaces respectively of the nail.

The proposed solutions are not controlled and are based mostly on the force of the material, which is adhered or attached to the nail, to restore its original state and by that to flatten the nail.

SUMMARY OF THE INVENTION

It is an object of the present invention to provide a device and method of therapeutic corrective treatment of toenail deformity.

It is another object of the present invention to provide a non-invasive device and method for treating ingrown nails.

It is yet another object of the present invention to provide a device and method for nail plate reforming that is controlled and adjustable over time.

It is therefore provided in accordance with a preferred embodiment of the present invention a device an adjustable and controllable device at least partially connected to an ingrown nail plate surface for treating ingrown nail, the device comprising:
    a releasing portion adapted to be connected to the ingrown nail plate surface;
    an adjustable portion adapted to exert changeable force on the releasing portion so as to elevate portions of the nail plate surface.

Furthermore and in accordance with another preferred embodiment of the present invention, said adjustable portion comprises:
    a supporting portion adapted to be glued substantially in an intact part of the plate surface;
    a resilient member connected between said adjustable portion and said releasing portion wherein the connection of said resilient member to said releasing portion is adjustable so that the force exerted by said resilient member on the said releasing portion is changeable Furthermore and in accordance with another preferred embodiment of the present invention, said releasing portion comprises a base and a flange and wherein said flange is adapted to be hooked to said resilient member.

Furthermore and in accordance with another preferred embodiment of the present invention, said supporting portion is provided with a flexible layer adapted to be placed between the nail plate and said supporting portion.

Furthermore and in accordance with another preferred embodiment of the present invention, said resilient member is a spring adapted to resiliently connect said releasing portion to said supporting portion.

Furthermore and in accordance with another preferred embodiment of the present invention, said adjustable portion is provided with a bar having at least one arm with two sides wherein one side is connected to said releasing portion and the other side is provided with height controller that changes the level of said arm relative to the nail plate surface.

Furthermore and in accordance with another preferred embodiment of the present invention, said bar is connected to said adjustable portion by a screw adapted to be released wherein the release action of the screw changes the force exerted by said bar on said releasing portion.

Furthermore and in accordance with another preferred embodiment of the present invention, said releasing portion comprises a base and a flange and wherein said flange is adapted to be hooked to said adjustable portion.

Furthermore and in accordance with another preferred embodiment of the present invention, said adjustable portion is provided with a spring that is adapted to be associated with said flange that is provided with a plurality of hooks adapted to maintain said spring in several positioning so as to change the force of the spring.

Furthermore and in accordance with another preferred embodiment of the present invention, said releasing portion is a magnet and said adjustable portion is another magnet adapted to exert attraction forces on said magnet.

Furthermore and in accordance with another preferred embodiment of the present invention, said adjustable portion is adapted to be placed opposite said magnet.

Furthermore and in accordance with another preferred embodiment of the present invention, said another magnet is connected above said magnet on a shoe or an insole.

Furthermore and in accordance with another preferred embodiment of the present invention, the device is further comprises a cage adapted to maintain a secured space around the toe.

It is therefore provided also in accordance with a preferred embodiment of the present invention, a method for treating ingrown nail comprising:

adhering a releasing portion on a toe's nail plate surface in an ingrown area;
providing an adjustable portion for exerting adjustable and controllable force on said releasing portion.

Furthermore and in accordance with another preferred embodiment of the present invention, the method further comprises adhering said adjustable portion to an intact portion of the nail's plate wherein said adjustable portion is provided with a spring and wherein the method further comprises associating said spring with said releasing portion.

Furthermore and in accordance with another preferred embodiment of the present invention, said releasing portion and said adjustable portion are made of magnetic materials.

BRIEF DESCRIPTION OF THE FIGURES

In order to better understand the present invention and appreciate its practical applications, the following Figures are attached and referenced herein. Like components are denoted by like reference numerals.

It should be noted that the figures are given as examples and preferred embodiments only and in no way limit the scope of the present invention as defined in the appending Description and claims.

FIGS. 7a-c illustrate a cross sectional view of magnetic-based device for treating ingrown nail in accordance with two versions of preferred embodiments of the present invention.

DETAILED DESCRIPTION OF THE FIGURES AND THE INVENTION

The proposed device and technology include application of adjustable and controlled device for nail plate reforming. The device action is preferably based on three principles:
I. Mechanical
II. Magnetic
III. Piezoelectric The adjustable device of the present invention provides a therapeutic (orthopedic) toenail deformity treatment. The device corrects the toenail deformity via constant dynamic corrective effort exerted on the lateral or/and medial edges of the toenail plate. According to one aspect of the present invention, mechanical instrument is illustrated.

Mechanical embodiments include an adjustable and controllable device for exerting a force on the upper external surface of a nail plate, wherein the device is adapted for attaching on the upper external surface of the nail plate only inside of the boundaries thereof, wherein the device comprises a releasing portion adapted to be attached to the upper external surface of a nail plate on a region in the vicinity of an ingrown nail plate farther from the rest of the intact part of the nail plate, and an adjustable portion adapted, by a mechanism based outside the region in the vicinity of the ingrown nail plate, to exert on the region in the vicinity of the ingrown nail plate via the releasing portion a changeable force directed and applied upwardly on and from above the region in the vicinity of the ingrown nail plate in a generally perpendicular orientation relative to the nail plate upper surface.

Figure 1:
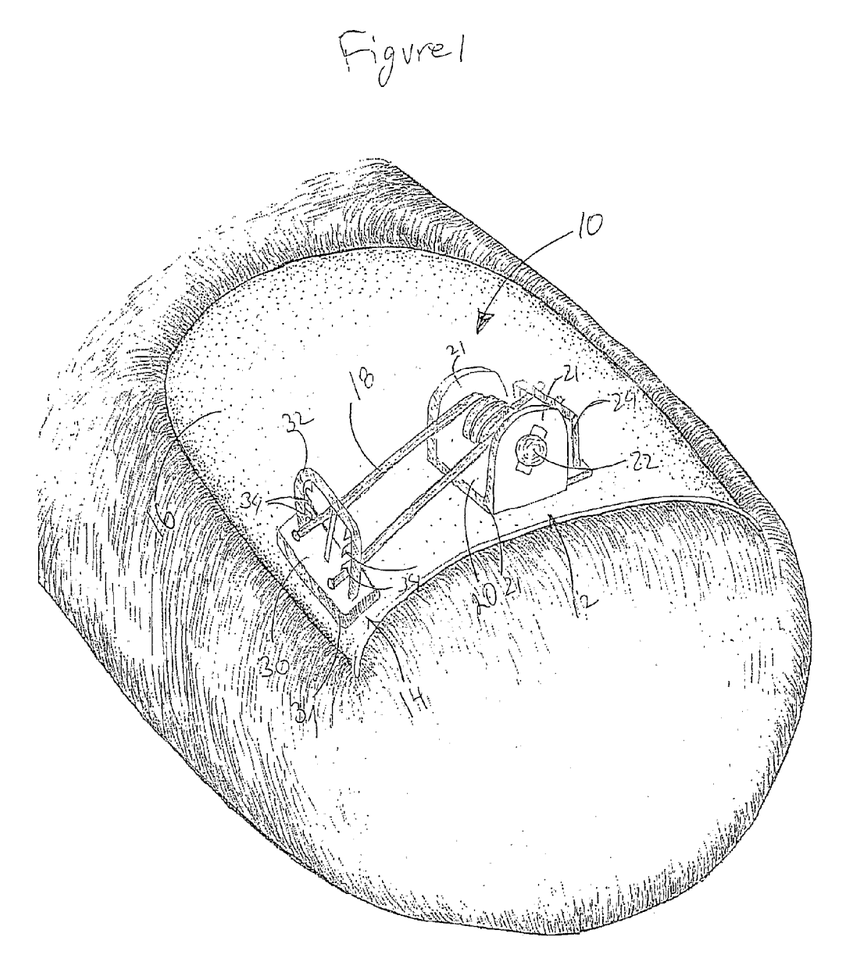
FIG. 1 illustrates a device for treating ingrown toenail in accordance with a preferred embodiment of the present invention.

Reference is now made to FIG. 1 illustrating a first mechanical version of a device for treating ingrown toenail in accordance with a preferred embodiment of the present invention. The device of the present invention is based solely on mechanical elements. Adjustable ingrown nail treatment device 10 comprises two main portions—a supporting portion 12 and a releasing portion 14. Both portions are glued to the nail's plate surface 16 while supporting portion 12 is glues substantially in the intact part of the nail plate surface 16 and releasing portion 14 is glued to the ingrown edge of the nail. Portion 12 and portion 14 are connected to one another by a resilient member 18 that pulls releasing portion 14 upwardly so as to lift the edge of the nail from the ingrown area.

Supporting portion 12 comprises a base 20, which is adapted to be glued to plate surface 16. Base 20 is provided with two opposite upright edges 21 that are adapted to hold a pin 22 therebetween to which resilient member 18 is connected. Base 20 is also provided with a flange 24 adapted to act as a hooking base to a portion of resilient element 18.

Releasing portion 14 is also provided with a base 30 adapted to be glued to the edge of plate surface 16. Base 30 is provided with a catch 32 that is adapted to hold the other side of resilient element 18. Catch 32 is provided with several hooks 34 adapted to maintain resilient element 18 in a several positions wherein in each positioning, different force is exerted on the nail's plate surface 18. This provides adjustability and controllability to the device of the present invention. The force that is exerted onto the plate is changed according to the repair stage of the ingrown nail and can be changed with time in accordance to the healing process.

It should be emphasized that both bases 20 and 30 are provided with flexible layers 21 and 31, respectively. The flexible layer is adapted to provide the device with a degree of freedom and adjustment so as to be affixed to any type, shape and texture of a toenail. Moreover, the flexible layers provide a simple means for the removal of the device that is performed by cutting the flexible layers.

Figure 2A:
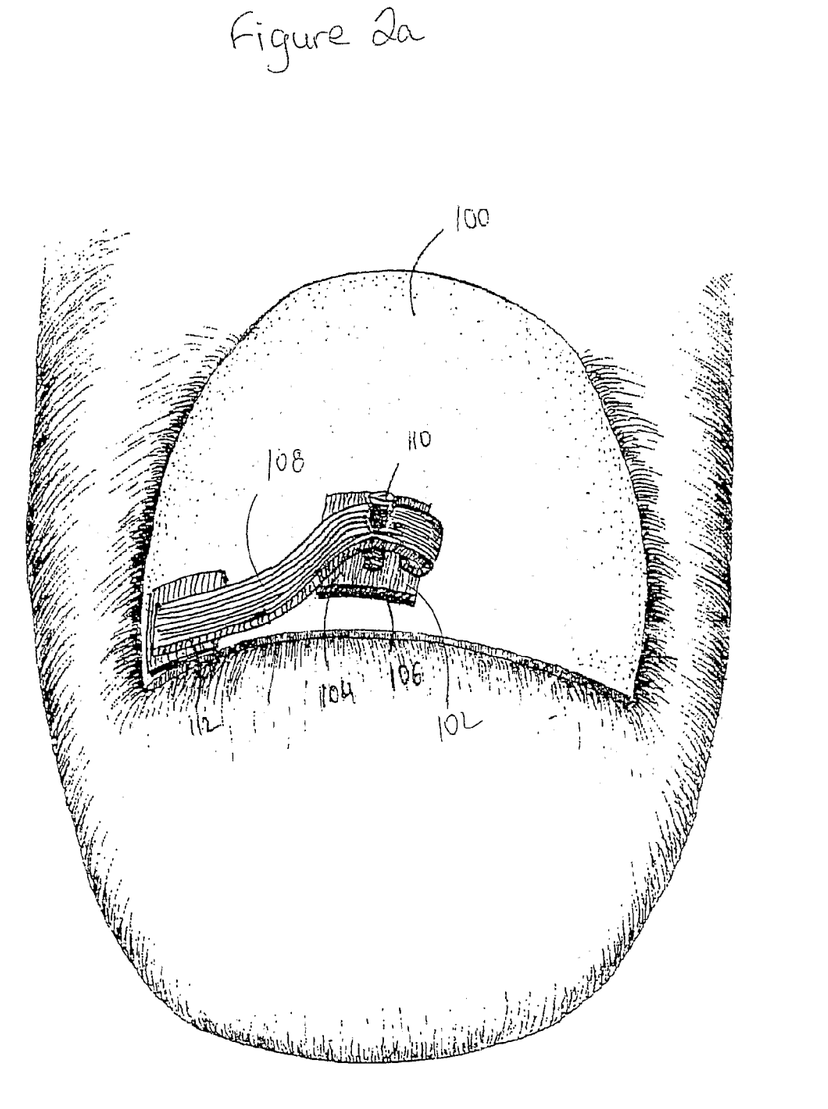
FIGS. 2a, b illustrate a device for treating ingrown toenail in accordance with another preferred embodiment of the present invention in two positions.
Figure 2B:
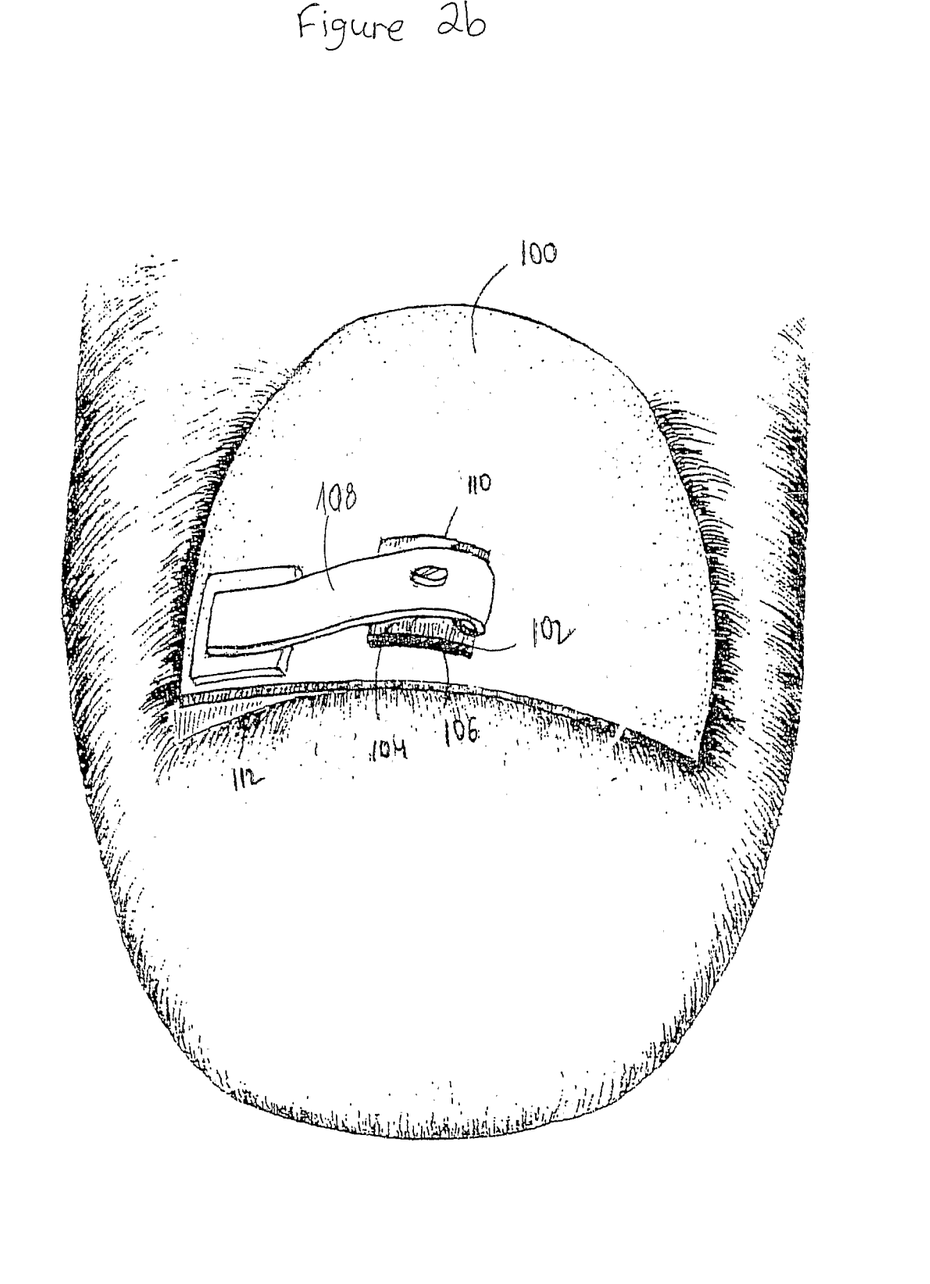

Reference is now made to FIGS. 2a and b illustrating another mechanical version of a device for treating ingrown toenail in accordance with another preferred embodiment of the present invention in two positions. FIG. 2a depicts a toenail's plate surface 100 onto which a device for treating an ingrown toenail 102 is provided. Device 102 comprises a base member 104 that is connected to plate surface 100 through a flexible layer 106 that facilitates the base to adhere to the toenail no matter what is the texture of the surface. Base member 102 is preferably glued to the nail plate substantially in its intact part and in accordance with the place of ingrown.

A bar 108 is connected to base member 102 through a screw 110. Bar 108 is connected at one end to base member 102 and at the other end, bar 108 is directed to an ingrown area of the toenail. The other end of bar 108 is connected by gluing in the vicinity of the ingrown area.

Bar 108 is provided with a flexible layer 112 adapted to be glued to surface plate 100. Bar 108 is adapted to level up the ingrown edge of the toenail so as to allow the inflammation beneath the surface to heal.

FIG. 2b illustrates a situation in which the end of bar 108 that is connected to the ingrown edge of the nail is being elevated so as to pull plate surface 100 of the nail and allow rapid healing of the inflammation beneath the ingrown part of toenail. Screw 110 is being screwed so as to adjust bar 108 to a predetermined force that is exerted on the toenail's plate surface.

Figure 3:
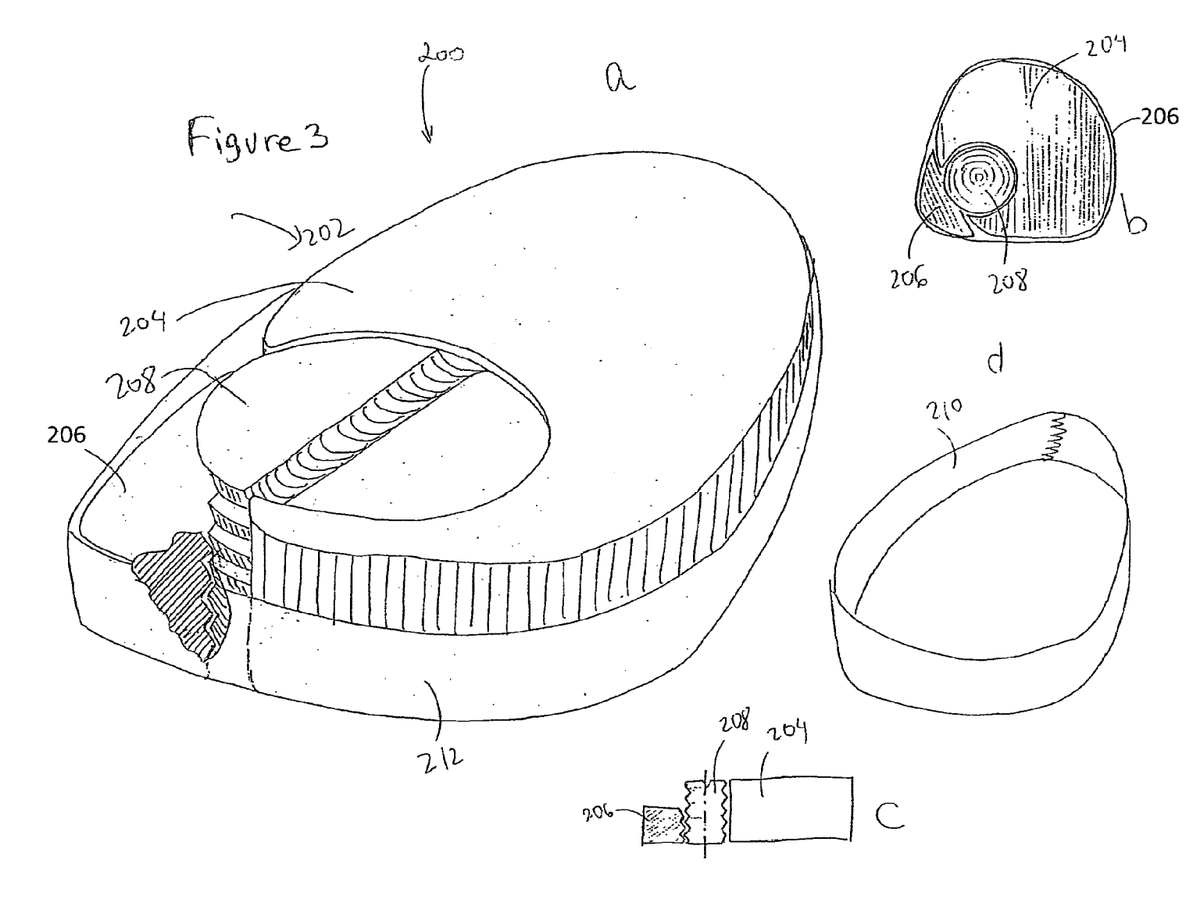
FIG. 3 illustrates a device for treating ingrown nail in accordance with yet another preferred embodiment of the present invention.

Reference is now made to FIG. 3 illustrating several views of a device for treating ingrown nail in accordance with yet another preferred embodiment of the present invention. Device 200 comprises two elements: a) supporting portion 202: including flankering part 204 that is fixed on the toe nail center and the toe nail intact part, b) releasing portion 206, fixed on the ingrown toenail angle; c) pinion rack driver 208, associated with supporting portion 204 and releasing portion 206, and d) cage 210 that is adapted to maintain all portions together.

Supporting portion 204 is preferably provided with a flexible layer adapted to provide an additional degree of freedom to the device and facilitate its removal.

In FIGS. 3a and 3c, it is shown that releasing portion 206 is provided with an outer thread that is associated with an opposite thread that is provided to pinion rack drive 208. When pinion rack drive 208 is screwed downwardly, releasing portion 206 is elevated while exerting force on the plate surface (the plate surface is not shown in FIG. 3). The exerted force on the toenail is controllable due to changeable force formed by screwing pinion rack drive 208.

Figure 4:
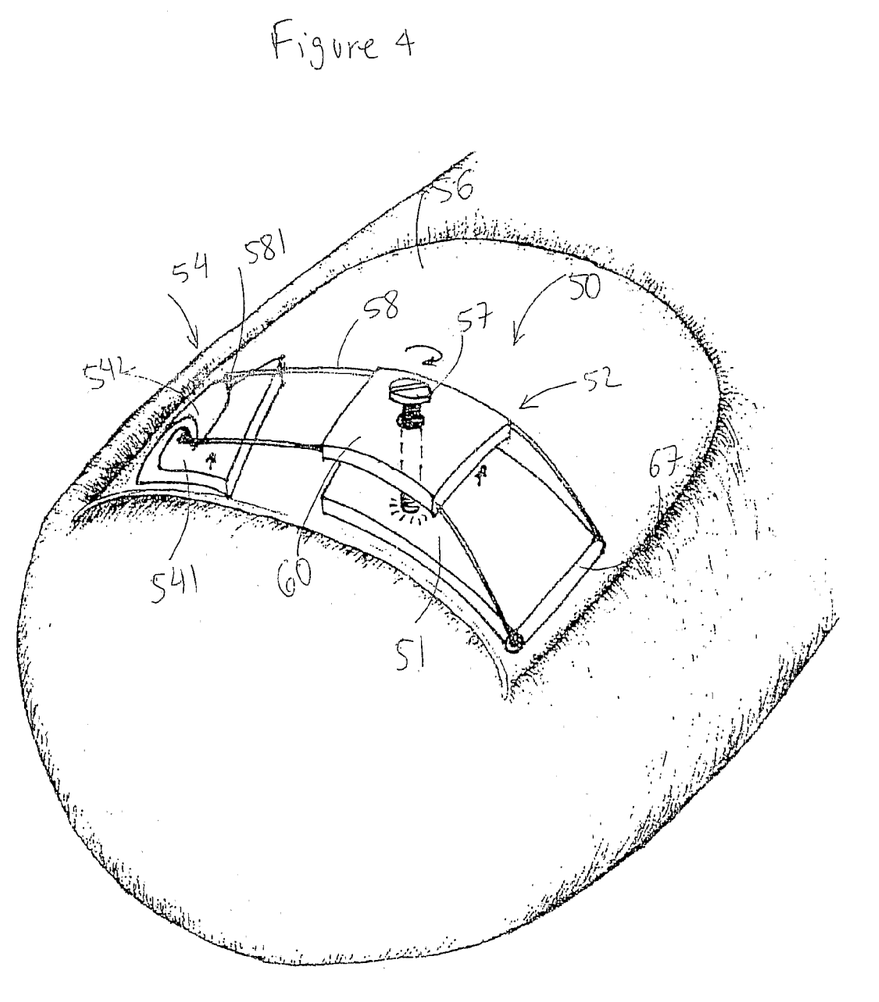
FIG. 4 illustrates an additional device for treating ingrown toenail in accordance with another preferred embodiment of the present invention.

Reference is now made to FIG. 4 illustrating an additional device for treating ingrown toenail in accordance with a preferred embodiment of the present invention. Device 50 of the present invention is based also on mechanical elements. Adjustable ingrown nail treatment device 50 comprises, two main portions—a supporting portion 52 and a releasing portion 54. Both portions are glued to a nail's plate surface 56 while supporting portion 52 is glued substantially in the intact part of nail plate surface 56 and releasing portion 54 is glued to the ingrown edge of the nail. Portion 52 and portion 54 are connected to one another by a resilient member 58 that pulls releasing portion 54 upwardly so as to lift the edge of the nail from the ingrown area.

Supporting portion 52 comprises a base 51 that is adapted to be glued to plate surface 56. Base 51 is supplied by hole, adapted to hold a screw 57 to which a plate 60 of resilient member 58 is connected. Base 51 is also provided with a flange 67 adapted to act as a connecting base to a portion of resilient element 58.

Releasing portion 54 is also provided with a base 541 adapted to be glued to the edge of plate surface 56. Base 541 is provided with a catch 542 that is adapted to hold a hook 581 of resilient element 58. Screw 57 can be positioned with different positioning in order to provide different force that is exerted on the nail's plate surface 56. This provides adjustability and controllability to the device of the present invention. The force that is exerted onto the plate is changed according to the repair stage of the ingrown nail and can be changed in time in accordance to the healing process.

It should be emphasized that both bases 51 and 541 are provided with flexible layers. The flexible layer is adapted to provide the device with a degree of freedom and adjustment so as to be affixed to any type, shape and texture of a toenail and simplify the device removal, which is performed by cutting the flexible layers.

Figure 5:
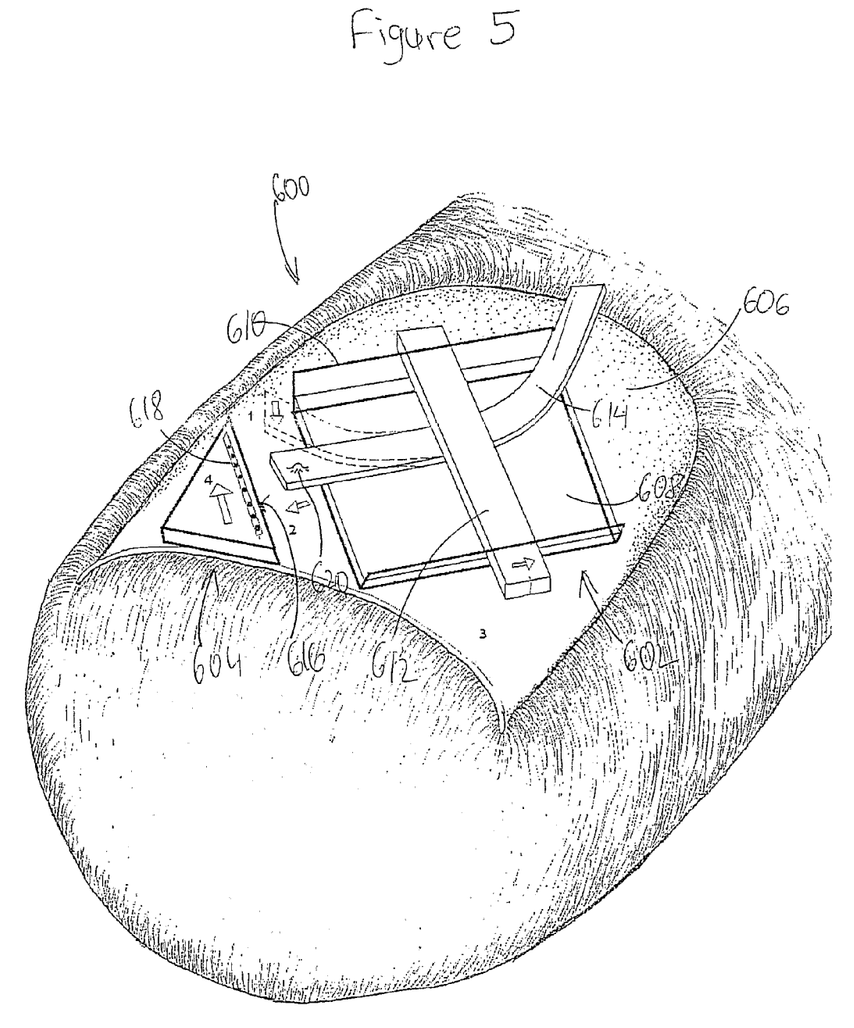
FIG. 5 illustrates another mechanical device for treating ingrown nail in accordance with yet another preferred embodiment of the present invention.

Reference is now made to FIG. 5 illustrating another mechanical device for treating ingrown nail in accordance with another preferred embodiment of the present invention. Device 600 comprises two portions: a force exerting portion 602 and releasing portion 604. Force exerting portion 602 is being fixed on the intact and substantially centered portion of plate surface 606 and releasing portion 604 is glues at the ingrown toenail angle.

Force exerting portion 602 comprises a base 608 having a frame made preferably using a square organized wire frame 610 that grasps a bar 612 that can be adjusted and moved backwardly as indicated by the arrow marked on the bar. A flat spring 614 is engages to be provided substantially perpendicular and beneath bar 612 so that the bar holds the level of the spring in a predetermined position fixed. Flat spring 614 is adapted to be moved along the frame made of wire 610 toward releasing portion 604

After both the releasing portion and the force exerting portion are glued to the nail's plate surface, spring 614, been previously passed through base frame, is being pushed towards releasing portion 604 and fixed into a recess 616. Flat spring 614 is provided with a protrusion 620 that is adapted to be inserted into a recess 618 from beneath so as to couple the spring to releasing portion 604.

The set of actions that are being performed are as follows: the spring is being directed downwardly toward the releasing portion (1) and then inserted within the releasing portion recess and the two portions are being couples (2). Then, the bar is being moved backwardly and away from the releasing portion (3) so as to elevate releasing portion of the nail (4) while exerting force on it.

Figure 6:
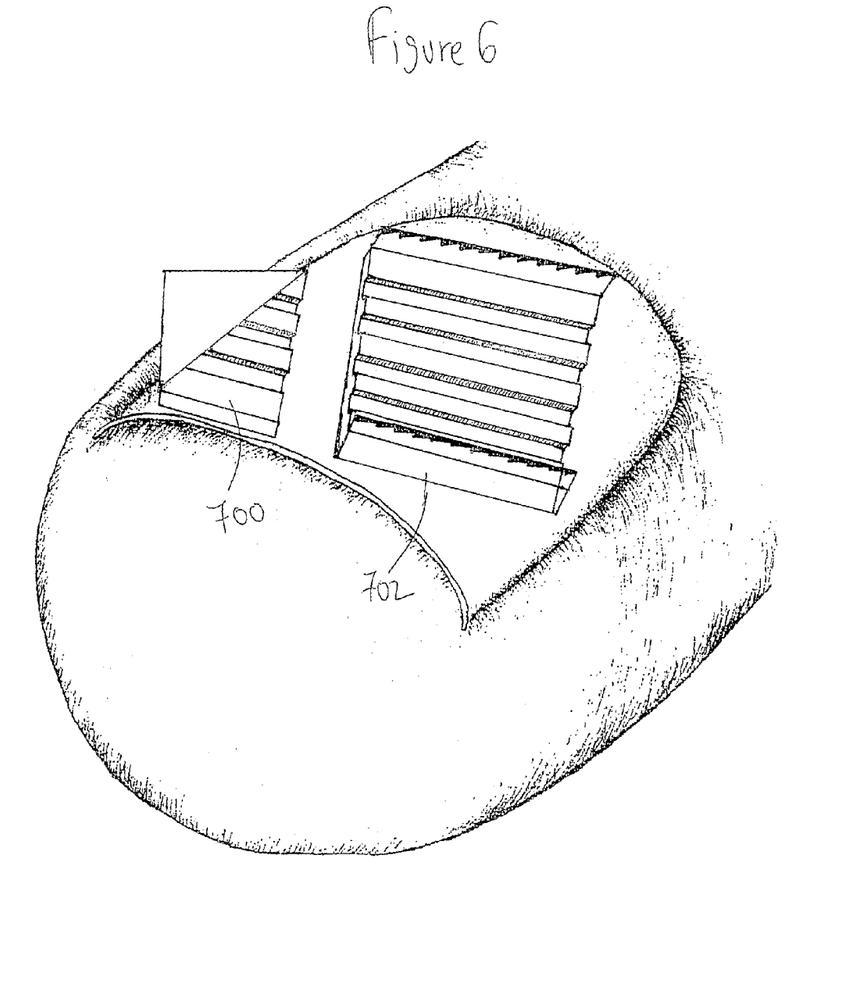
FIG. 6 illustrates another version of the embodiment shown in FIG. 5.

Reference is now made to FIG. 6 illustrating another version of the device shown in FIG. 5. In this embodiment, several springs can be utilized and therefore, releasing portion 700 (that is partially cross sectioned) and supporting portion 702 have several rails for inserting several springs so as to gain control over the force exerted on the nail's plate surface.

The examples given in FIGS. 1 to 6 illustrate examples of mechanical type of the device of the present invention in which the resilient element is adapted to change the force exerted onto the plate surface as mentioned herein before. This is one of the aspects of the present invention. Other mechanical devices can be designed and constructed such as a device whose exerted force is adjusted by a ratched gearing (ratched-and-pawl/rack) mechanism that is adapted to reach and keep resilient element stretching. Other mechanical devices can be designed by person skilled in the art. The designs will be covered by the scope of the present invention.

In accordance with another aspect of the present invention, magnetic element can be utilized.

Figure 7A:
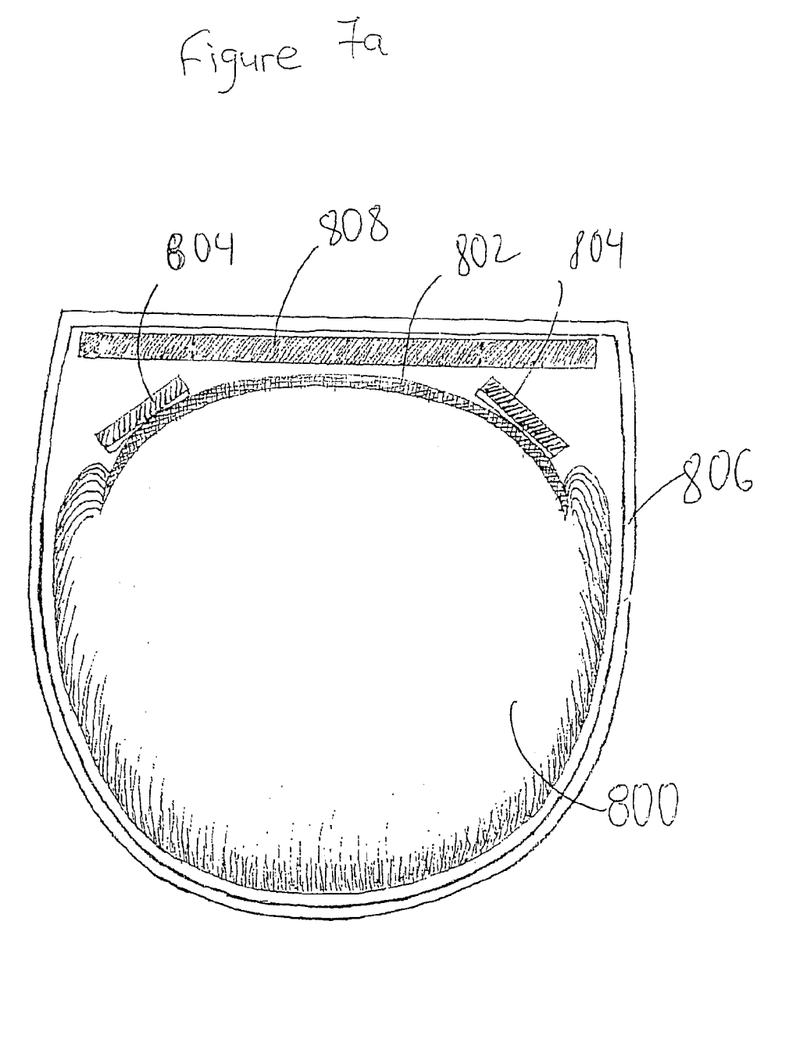

Reference is now made to FIG. 7 illustrating a cross sectional view of a magnetic-based device for treating ingrown nail. Nail 802 of toe finger 800 is provided with one (FIG. 7b) or two (FIG. 7a) magnetic elements that are being glued to the edge of the nail that is being ingrown. A cage 806 that is adapted to surround finger 800 is provided with an opposite magnet 808 in the upper portion, facing nail 802. FIG. 7b illustrates a finger places within a shoe 812 that is provided with magnet 810, wherein an opposite magnetic element 804 is adhered onto the nail in the ingrown area. The upper magnetic element, either 808 or 810, respectively, is exerting magnetic attraction force on magnetic elements 804 that are glued to the nail. The force that is exerted onto the glued magnetic elements elevates the nail off the finger so as to release the ingrown edge of the nail.

Figure 7C:
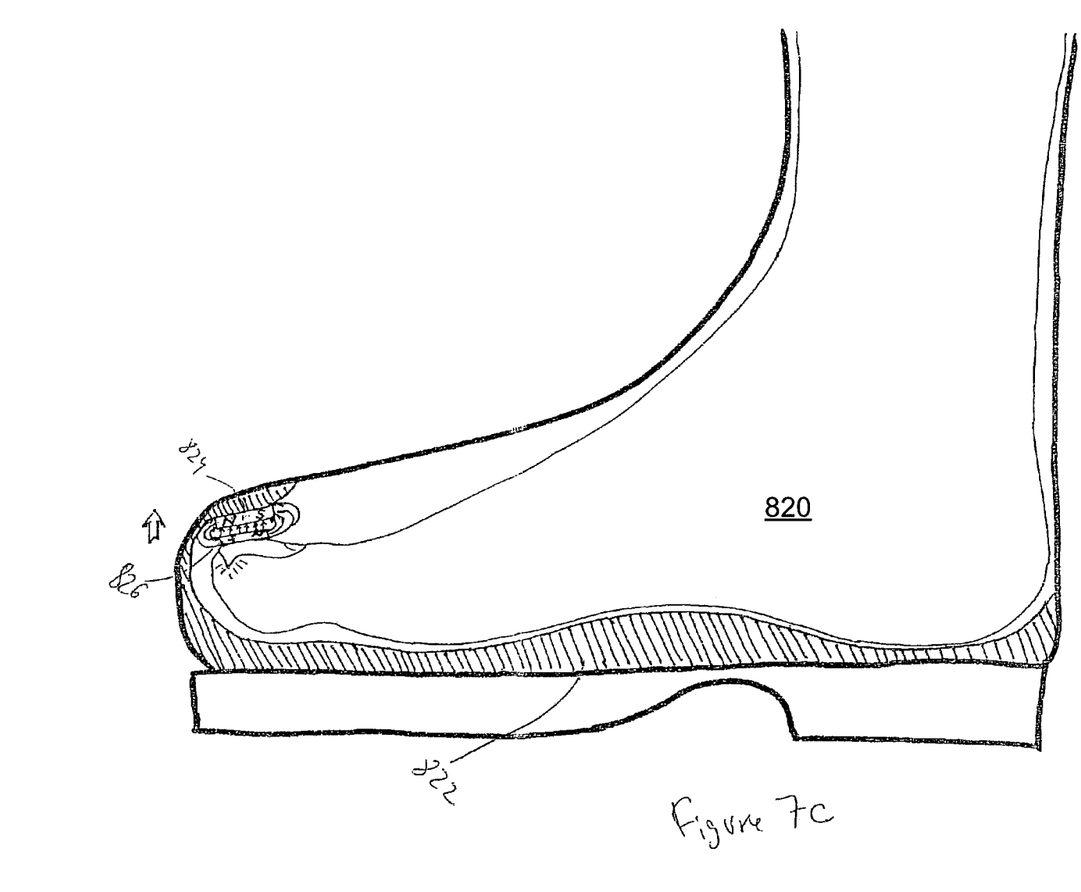

FIG. 7c illustrates a leg 820 places within a shoe 822 that is provided with magnetic element 824. The device is operated in the following manner: During walking, the big toe presses on its plantar surface in the step stage, when forefoot is the weight bearing part of lower extremity (push off). The big toe in this moment makes movement directed downwards and magnetic field stretches ingrown toe nail corner "up" in the direction toward a second magnet 826, thus step-by-step performing repair of the ingrown nail corner.

Figure 8A:
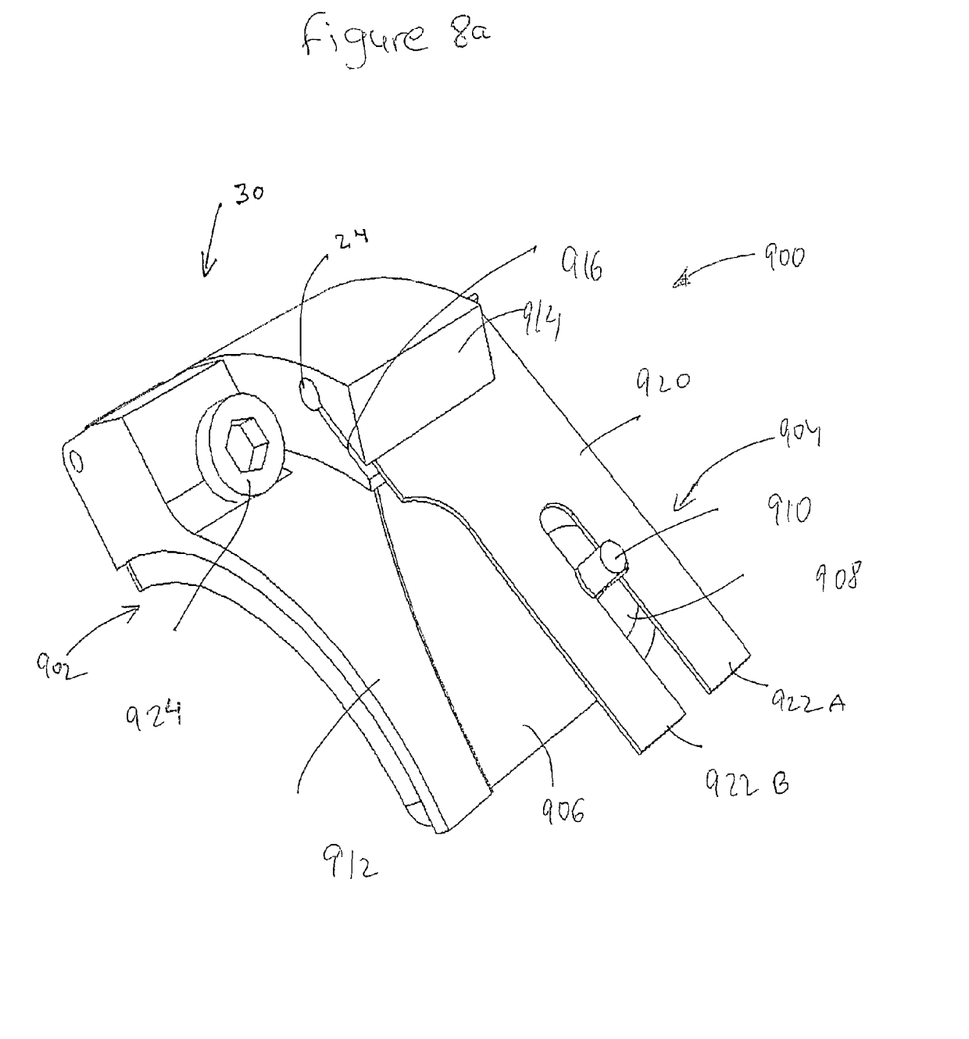
FIGS. 8a,b illustrates two views of a mechanical-based device for treating ingrown nail in accordance with yet another preferred embodiment of the present invention.
Figure 8B:
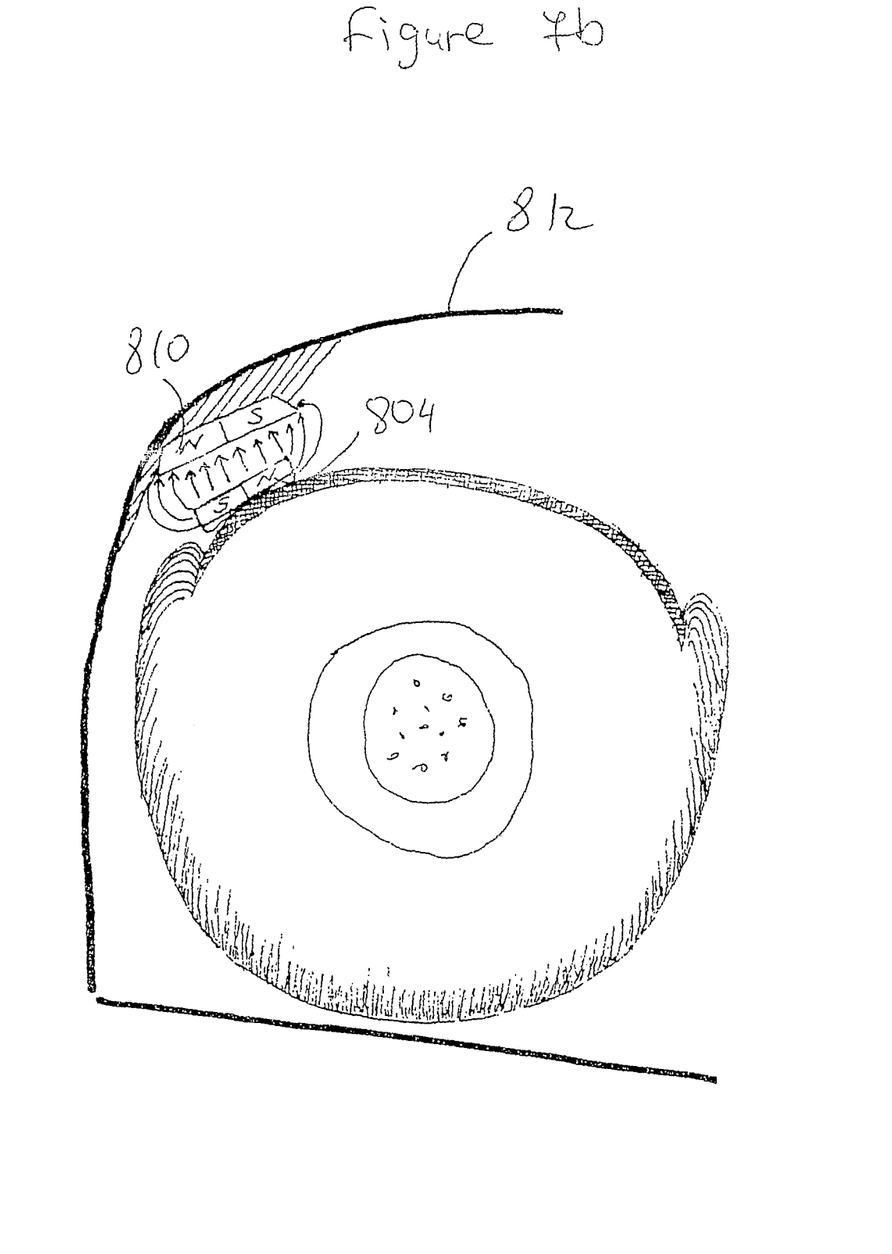

Reference is now made to FIGS. 8a and b illustrating two views of a mechanical-based device for treating ingrown nail in accordance with yet another preferred embodiment of the present invention. Device 900 comprises a supporting portion 902 and a releasing portion 904. Releasing portion 904 is glued on the nail plate 906 in the ingrown area through a base 908 and is provided with a flange 910. Supporting portion 902 comprises a base 912 and an adjacent lever 914. Lever 914 is provided with a slot 916 by which a spring 920 is provided wherein the free end of the spring is provided with a bifurcated portion 922a and 922b that are adapted to be held by flange 910 of releasing portion 904 and pulls flange 910 upwardly.

A screw 924 is provided to supporting portion 902 that is controlling the amount of force that is being exerted on spring 920.

Types I (mechanical) and type II (magnetic) of devices realize their action through the resilient element, which can be brakes/braces attached to the nail's plate surface. In type I, mechanical connective element performs the effort of toenail re-formation. In type II version of the device, magnetic field acts as connective element providing efforts, needed for toenail re-formation type III of the device of the present invention performs its action through piezoelectric effect. Plane piezoelectric element, cut out according to patient's nail size and ingrown nail edge location, is glued to the nail plate surface, with following changes in piezoelectric element's form due to step-by-step electric impulses thus causing of connected toenail re-forming.

It should be noted that any other physical law can be utilized in order to force a member that is glued to the nail plate in the ingrown are to be raised in a controlled manner without limiting the scope of the present invention.

It should be noted also that any method for gluing the portions of the device to the nail's plate surface can be used without limiting the scope of the present invention.

The method by which the device of the present invention is being applied is as follows:

Foot bath with soap and, optionally, nail softening material;

Filing down the toe-nail surface of normal nail part or correcting the line of the supposed toe-nail deformity;

Forming a flat surface on the nail for attachment of the elements of the devices that are described herein before;

Gluing the first portion on safe normal and intact part of the toe-nail;

Gluing the second portion with attached resilient element on the ingrown part of the toe-nail;

Binding the resilient element between the two portions;

Stretching the spring or wire or any other element as shown herein before until the patient feels some relief of toeache and locking the resilient element so as to establish a predetermined force;

Covering the toe and device with cage (for non-plane types of device);

Correcting step-by-step from time to time the force exerted by the resilient element for reforming the ingrown toenail.

Action of springs as resilient elements is more prolonged and obviously do not demand everyday correction, which may be fulfilled by addition of springs or their substitution by more stressed ones.

The devices that are designed to have a plane profile that does not substantially protrude of the nail do not demand a cage.

In accordance with the method of the present invention, the method can include also preliminary filling down of nail plate with the help of abrasion; preliminary partial or complete cutting of deformed toe nail' plate; preliminary softening of deformed toe-nail' plate with the help of warm soap bath; or preliminary softening of deformed toe nail' plate with the help of chemical agents action.

Additional and optional technologies that can be implemented in addition to the main method:

Optionally, artificial nails can be used as a basis for the supporting portion of the device;

Optionally, the supporting portion also may be diestamped from the material, used for artificial nails production.

Optionally, modeling of the glued surface of the resilient portion basis with a drilling engine according to the form of the external part of the ingrown nail which form must be corrected.

Optionally, casting of the external part of the ingrown nail can be performed for making individual resilient element basis with full accordance of the glued surfaces to the basis and the toenail plate.

Optionally, abrasion of the toenail plate from ⅓ to ⅔ of its thickness so as to be even on the border of stable and moving braces.

As shown, for example, in FIG. 1, FIGS. 2A-2B and FIGS. 4-5, it is noted and emphasized that devices described herein are placed on the upper external surface of the nail's plate only inside of or within the boundaries thereof and apply a changeable force generally perpendicular to the nail's plate upper surface.

It should be clear that the description of the embodiments and attached Figures set forth in this specification serves only for a better understanding of the invention, without limiting its scope as covered by the following claims.

It should also be clear that a person skilled in the industry, after reading the present specification can make adjustments or amendments to the attached Figures and aforementioned embodiments that would still be covered by the following claims.

The invention claimed is:

1. An adjustable and controllable device for exerting a force on an upper external surface of a nail plate, wherein the device is adapted for attaching on the upper external surface of the nail plate only inside of the boundaries thereof, the device comprising:
   a releasing portion adapted to he attached to the upper external surface of the nail plate on a region in the vicinity of an ingrowth of the nail plate;
   an adjustable portion based outside the region in the vicinity of the ingrowth of the nail plate, adapted to exert the force directed upwardly from the region in the vicinity of the ingrowth of the nail plate in a generally perpendicular orientation relative to the upper external surface so as to elevate the nail plate, and a shoe;
   wherein said releasing portion is a first magnet and said adjustable portion is a second magnet wherein the force comprises magnetic attraction exists between said first magnet and said second magnet, and wherein said second magnet is within said shoe.

2. A method for exerting a force on an upper external surface of a nail plate, comprising:
   providing, an adjustable and controllable device adapted for attaching on the upper external surface of the nail plate only inside of the boundaries thereof and said device having a releasing portion and an adjustable portion;
   adhering the releasing portion on the upper external surface of the nail plate only inside of the boundaries thereof and in the vicinity of an ingrowth of the nail plate;
   connecting the adjustable portion to said releasing, portion, thereby exerting on the ingrowth of the nail plate the force directed upwardly from above the region in the vicinity of the ingrowth of the nail plate in a generally perpendicular orientation relative to the nail plate upper surface so as to elevate the nail plate,
   providing a shoe wherein said releasing portion and said adjustable portion are made of magnetic materials wherein the force comprises magnetic attraction exists between said first magnet and said second magnet, and wherein said second magnet is within said shoe.

* * * * *